United States Patent [19]
Alt et al.

[11] Patent Number: 5,710,224
[45] Date of Patent: *Jan. 20, 1998

[54] METHOD FOR PRODUCING POLYMER OF ETHYLENE

[75] Inventors: Helmut G. Alt, Bayreuth, Germany; Syriac J. Palackal, Bartlesville, Okla.; M. Bruce Welch, Bartlesville, Okla.; David C. Rohlfing, Bartlesville, Okla.; Jay Janzen, Bartlesville, Okla.

[73] Assignee: Phillips Petroleum Company, Bartlesville, Okla.

[*] Notice: The term of this patent shall not extend beyond the expiration date of Pat. No. 5,436,305.

[21] Appl. No.: 399,119

[22] Filed: Mar. 3, 1995

Related U.S. Application Data

[63] Continuation-in-part of Ser. No. 734,853, Jul. 23, 1991, Pat. No. 5,436,305, Ser. No. 17,207, Feb. 12, 1993, Pat. No. 5,411,925, and Ser. No. 154,224, Nov. 17, 1993, Pat. No. 5,466,766.

[51] Int. Cl.$^6$ .................... G08F 4/64; G08F 10/02
[52] U.S. Cl. .................... 526/160; 526/132; 526/134; 526/170; 526/348.3; 526/347.5; 526/347.6; 526/352
[58] Field of Search ............... 526/160, 170, 526/132, 134, 348.3, 348.5, 348.6, 352

[56] References Cited

U.S. PATENT DOCUMENTS

| | | | |
|---|---|---|---|
| 5,272,236 | 12/1993 | Lai et al. | 526/348.5 |
| 5,278,272 | 1/1994 | Lai et al. | 526/348.5 |
| 5,391,789 | 2/1995 | Rohrmann | 526/160 X |
| 5,422,409 | 6/1995 | Brekner et al. | 526/160 X |
| 5,436,305 | 7/1995 | Alt et al. | 526/126 X |

FOREIGN PATENT DOCUMENTS

| | | |
|---|---|---|
| 2017190 | 11/1990 | Canada . |
| 2075550 | 2/1993 | Canada . |
| 399 348 A2 | 5/1990 | European Pat. Off. . |
| 604 908 A2 | of 1993 | European Pat. Off. . |
| 524624 A2 | 1/1993 | European Pat. Off. . |
| 690079 | 1/1996 | European Pat. Off. . |
| WO 94/07930 | 4/1994 | WIPO . |

OTHER PUBLICATIONS

Kaminsky, "Metallocene Catalysts," SP'92–Polyethylene World Congress, Dec. 7–9, 1992, Zurich, CH.

Derwent Abstract for PCT 94/19381.

Derwent Abstract for EPC 399,348.

*Makromol. Chem.* 193, 1359–1367 (1992).

*Makromol. Chem.* 194, 3167–3182 (1993).

*Primary Examiner*—Fred Teskin
*Attorney, Agent, or Firm*—Edward L. Bowman

[57] ABSTRACT

A process for preparing a polymer of ethylene having a flow activation energy higher than that of a substantially linear ethylene polymer of the same molecular weight involving using bridged sandwich-bonded fluorenyl-containing metallocenes and the polymers resulting therefrom.

25 Claims, No Drawings

METHOD FOR PRODUCING POLYMER OF ETHYLENE

This application is a continuation-in-part of application Ser. No. 07/734,853 filed Jul. 23, 1991, now U.S. Pat. No. 5,436,305; and a continuation-in-part of application Ser. No. 08/017,207 filed Feb. 12, 1993, now U.S. Pat. No. 5,411,925; and a continuation-in-part of U.S. application Ser. No. 08/154,224 filed Nov. 17, 1993, now U.S. Pat. No. 5,466,766. The disclosures of all three of those applications are incorporated herein by reference.

BACKGROUND OF THE INVENTION

The present invention relates to polymers of ethylene. Polyethylene producers have spent considerable time and money over the years trying to produce polyethylene polymers that can be processed over a wide range of conditions while producing a wide range of mechanical property characteristics. Accordingly, processes have been developed for producing high density polyethylenes, linear low density polyethylenes, very low density polyethylenes, and even ultra low density polyethylenes. Much of the catalyst research has been directed toward finding ways to modify the molecular architecture of the polymer molecules so as to extend the boundaries of the characteristics of the polymers.

At the two extremes of commercial polyethylenes one has linear polyethylenes (LPE) and "conventional" low density polyethylene (LDPE). The low density polyethylenes have been traditionally produced by free-radical polymerization of ethylene in high temperature, high pressure reactors using peroxide initiators. The polymer molecules in "conventional" low density polyethylenes are generally viewed as having high levels of long chain branching along the polymer chains. It is also considered that many of the long chain branches also have high levels of branching. The long branching of these low density polyethylenes provides polymer melt properties that are advantageous for some types of applications. However, large amounts of long chain branching can also result in polymers have less than desirable physical properties for some applications. For example LDPE generally has lower stiffness, hardness, tear resistance, and tensile strength than do linear polyethylenes of equivalent density and melt index.

The polymers generally referred to as linear polyethylenes have typically been produced by addition polymerization of ethylene or copolymerization of ethylene and other alpha-olefin comonomers. Various processes have been developed including methods using chromium oxide catalysts or coordination catalysts based on the combination of certain transition metal compounds and metal alkyls.

The coordination catalysts such as those of the early work of Ziegler and Natta are generally referred to as multisite catalysts for the reason that those catalyst systems appear to have a number of types of active sites which result in the production of polymer molecules having a wide range of molecular weights. The polymer molecules can also have a wide range of comonomer distribution, also often referred to as compositional distribution. The polymers produced with such coordination catalysts generally have different physical properties and processability characteristics than polymers produced using the chromium based catalyst systems developed by Phillips Petroleum Company.

The multisite coordination metal catalysts are thought to produce substantially linear polymer molecules having a relative wide range of molecular weights but little long chain branching and minimal amounts of terminal vinyl groups. In contrast, the chromium based catalyst systems produce polymer molecules having higher degrees of long chain branching and more terminal vinyl groups. The shear stress response, i.e HLMI/MI, for polymers produced using the chromium catalyst systems is generally 60 or more, whereas for polymers produced with the coordination catalysts, it is generally around 30. Similarly, the chromium catalyst systems can produce polymers having flow activation, i.e. Ea values of 30 kJ/mole or more whereas polymers of similar molecular weight produced with the coordination catalysts have Ea values of less than 30. The natural balance of short and long chain branching in the polymers produced using the chromium catalysts provides them with a balance of processing and mechanical advantages that are often not provided by the polymers produced using the coordination catalysts. Because of the lack of long chain branching in the polymers produced with the coordination catalysts, the polymers have in some cases been subjected to further reaction with free radical initiators to introduce some branching to improve the processability of the polymers. In addition the polymers produced with the coordination catalyst systems often contain significant levels of chloride residual which can be undesirable in some applications.

Some of the current excitement regarding using metallocenes as polymerization catalysts stems from the fact that, while metallocenes can be viewed as transition metal compounds, as a result of their particular molecular composition, metallocenes have been at least theorized as being capable of producing "single site" catalysts which will produce polymer molecules having more structural uniformity than polymer molecules produced using the multisite coordination catalyst systems of the type that has been used commercially for years.

The concept of using metallocenes such as bis (cyclopentadienyl) titanium, zirconium, or vanadium was known in the 1950's. Some of the early work used those materials in combination with alkylaluminum cocatalysts of the type usually used with current commercial coordination catalyst systems. Those were generally viewed as not having sufficient activity to be of commercial importance. Later is was found that such metallocenes when combined with an aluminoxane cocatalyst would be more active. The resulting polymers generally had a narrow molecular weight distribution, i.e. HI's of less than 4, and little if any long chain branching, i.e. low flow activation energy values and low shear stress response values. However, the molecular weights of these polymer molecules were not always of the level desired for good mechanical properties and the absence of any significant amount of long chain or short chain branching resulted in polymers having some of the same limitations as those produced using the coordination catalysts. It appears that for the best combination of processability and polymer mechanical properties, it would be desirable for polymers to have a proper balance of long and short chain branching and molecular weight distribution.

One object of the present invention is to provide a method for producing ethylene polymers with a metallocene wherein the polymers have better processing characteristics than a substantially linear ethylene polymer of the same weight average molecular weight.

Another object of the present invention is to provide a polymer of ethylene having long chain branching while not containing Ti, Cr, or remnants of peroxide, i.e materials contained in most all current commercial polyolefins.

SUMMARY OF THE INVENTION

In accordance with the present invention, there is provided a process for preparing a polymer of ethylene having a flow activation energy of at least about 25 kJ/mol comprising contacting ethylene in a liquid diluent with a catalyst system comprising:

(1) a catalyst comprising a bridged sandwich-bonded metallocene having two cyclopentadienyl-type groups attached to the bridging structure, wherein both said cyclopentadienyl-type groups are sandwich bonded to the metal of the metallocene, and wherein at least one of said cyclopentadienyl-type groups attached to the bridge is a substituted or unsubstituted fluorenyl group and, (2) a suitable cocatalyst, the currently preferred cocatalyst being an aluminoxy co-catalyst having repeating units of the formula

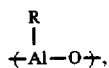

wherein, R is a hydrocarbyl group.

A further object of the present invention is to provide new polymers of ethylene which have a higher flow activation energy than a substantially linear polyethylene having the same weight average molecular weight.

Still another object of the present invention is to provide new polymers that have a higher flow activation energy than those which can be produced using conventional coordination catalysts or chromium catalysts.

Still yet another object of the present invention is to provide a method for producing very high flow activation energy polymers, i.e. highly branched polymers, that do not contain any remnants of the organic peroxide catalysts that are generally present in free radical-modified polyethylenes. Some of these polymers have a zero shear viscosity at 190° C. such that $\eta_o/M_w^{3.4} > 20(10^{-13})$, and typically $\eta_o/M_w^{3.4} < 20(10^{-6})$.

Still another object of the present invention is to provide a low pressure method for producing low density polymers having flow activation energy values similar to those of high pressure LDPE.

DETAILED DESCRIPTION OF THE INVENTION

The term "substantially linear ethylene polymer" as used herein refers to polymers of ethylene having no more than about 3 long chain branches 1000 carbon atoms. The term long chain as used herein refers to chains having 6 or more carbon atoms. Long chain branching can be determined using $C^{13}$ nuclear magnetic resonance (NMR) spectroscopy and is quantified using the method of Randall (*Rev. Macromol. Chem. Phys.*, C29 (2&3), p. 285–297), the disclosure of which is incorporated herein by reference. The presence of long chain branching is also reflected if there are significant differences observed for molecular weight values obtained using a relative refractive index detector and a low angle light scattering detector on a given molecular weight fraction of a polymer.

The term "bridged metallocene" as used herein refers to a metallocene in which two cyclopentadienyl-type groups are connected by a bridging structure. The term "sandwich bonded metallocene" refers to those metallocenes in which both of the cyclopentadienyl-type groups attached to the bridge are bonded to the transition metal of the metallocene. Cyclopentadienyl-type groups refer to organic groups containing cyclopentadienyl structures such as cyclopentadienyl, fluorenyl, indenyl, tetrahydroindenyl, benzofluorenyl, octahydrofluorenyl, and substituted variations thereof.

The bridged metallocenes employed in the present invention are fluorenyl-containing metallocenes. Unless specifically noted elsewhere, the bonding of the fluorenyl to the bridge is through the 9 position on the fluorenyl. Such fluorenyl-containing metallocenes include compounds of the formula (Z)—R'—(Z')MeQ$_k$ wherein R' is an organo group linking Z and Z', Z is a substituted or unsubstituted fluorenyl radical, Z' is a substituted or unsubstituted fluorenyl radical, a substituted or unsubstituted indenyl radical, a substituted or unsubstituted cyclopentadienyl radical, a tetrahydroindenyl radical, a substituted or unsubstituted benzofluorenyl radical, or an octahydrofluorenyl radical. The substituents on Z and Z' can be selected from generally any substituents which do not preclude the metallocene from having the desired activity. Hydrocarbyl substituents having 1 to 20 carbons are common. Me is a transition metal selected from the elements of Groups IVB, VB, or VIB of the Periodic Table. Each Q can be the same or different and can be selected from a monovalent group consisting of hydrogen, halogen, a hydrocarbyl group having 1 to 20 carbon atoms, an alkoxy group having 1 to 20 atoms, an amino group which may or may not be substituted with up to two hydrocarbyl groups having 1 to 20 carbons, a phosphorus-containing hydrocarbyl group having 1 to 20 carbon atoms, and a silicon-containing hydrocarbyl group having 1 to 20 carbons, and an aluminum-containing hydrocarbyl group having 1 to 20 carbon atoms. In particularly preferred embodiments Z' is selected from substituted or unsubstituted indenyl radicals.

Some examples of what is meant by the R' bridging groups include hydrocarbyl alkylene radicals, divalent dihydrocarbyl germanium radicals, divalent dihydrocarbyl silyl radicals, divalent hydrocarbyl phosphine radicals, divalent hydrocarbyl amine radicals, and divalent dihydrocarbyl tin radicals. Still more examples are provided in U.S. Pat. No. 5,087,677 column 5, lines 10–45. Still others are disclosed in U.S. Pat. No. 4,975,403 column 4, lines 15–26 and U.S. Pat. No. 5,132,381 column 2, lines 41–65. Included are R' groups containing as few as one carbon atom to 20 carbon atoms or more.

A number of examples of such bridged fluorenyl-containing metallocenes and methods for preparing them are disclosed in commonly owned published European Application No. 524,624. Some specific examples of sandwich bonded bridged fluorenyl-containing metallocenes in which Me is zirconium and each Q is chloride include:

1) 1-(fluorenyl)-1-(cyclopentadienyl) methane zirconium dichloride,
2) 1-(fluorenyl)-1-(indenyl) methane zirconium dichloride,
3) 1-(2,7-di-t-butylfluorenyl)-1,1-(dimethyl)-1-(cyclopentadienyl) methane zirconium dichloride,
4) 1-(2,7-di-bromofluorenyl)-1,1-(dimethyl)-1-(cyclopentadienyl) methane zirconium dichloride,
5) 1-(2,7-di-methylfluorenyl)-1,1-(dimethyl)-1-(cyclopentadienyl) methane zirconium dichloride,
6) 1-(2,7-di-phenylfluorenyl)-1,1-(dimethyl)-1-(cyclopentadienyl) methane zirconium dichloride,
7) 1-(2,7-diphenylfluorenyl)-1,1-(diphenyl)-1-(cyclopentadienyl) methane zirconium dichloride,
8) 5-(fluorenyl)-5-(cyclopentadienyl)-1-hexene zirconium dichloride,
9) 1-(2,7-di-t-butylfluorenyl)-1,1-(diphenyl)-1-(cyclopentadienyl) methane zirconium dichloride,
10) 1-(fluorenyl)-1-(cyclopentadienyl)-1-(n-butyl)-1-(methyl) methane zirconium dichloride,
11) 1-(2,7-dichlorofluorenyl)-1,1-(diphenyl)-1-(cyclopentadienyl) methane zirconium dichloride,
12) 1-(fluorenyl)-1-(cyclopentadienyl) cyclopentane zirconium dichloride,
13) 1-(fluorenyl)-1-(cyclopentadienyl)-1-(3-cyclohexenyl) methane zirconium dichloride,
14) 1-(fluorenyl)-1(3-allylcyclopentadienyl)-1,1-(dimethyl) methane zirconium dichloride,
15) 1-(2,7-di-methylvinylfluorenyl)-1-(cyclopentadienyl)-1,1-(dimethyl) methane zirconium dichloride,
16) 1-(fluorenyl)-1-(3-trimethylsilylcyclopentadienyl)-1,1-(dimethyl) methane zirconium dichloride, 17) 1-(fluorenyl)-1-(cyclopentadienyl)-1-(para-methoxyphenyl) methane zirconium dichloride,
18) bis(1-methylfluorenyl) methane zirconium dichloride,
19) 1-(fluorenyl)-1-(cyclopentadienyl)-1-(phenyl)methane zirconium dichloride,
20) 2-(fluorenyl)-2-(cyclopentadienyl)-(adamantyl) zirconium dichloride,
21) 1-(2,7-di-mesitylfluorenyl)-1-(cyclopentadienyl)-1,1-(dimethyl) methane zirconium dichloride,
22) 1-(2-phenylfluorenyl)-1,1-(dimethyl)-1-(cyclopentadienyl) methane zirconium dichloride,
23) 1-(2,7-dimethoxyfluorenyl)-1,1-(diphenyl)-1-(cyclopentadienyl) methane zirconium dichloride,
24) 1-(2,7-dimesitylfluorenyl)-1-(cyclopentadienyl) cyclopentane zirconium dichloride,
25) 1-(2,7-diphenylfluorenyl)-1-(cyclopentadienyl)-1-(phenyl) methane zirconium dichloride,
26) 1-(3,4-dimethylfluorenyl)-1-(cyclopentadienyl)-1-(phenyl) methane zirconium dichloride,
27) 1-(fluorenyl)-2-(indenyl) ethane zirconium dichloride, also known as 1-(fluorenyl)-2-(indenyl) ethylene zirconium dichloride,
28) 1-(4-methylfluorenyl)-2-(1-methylfluorenyl) ethane zirconium dichloride,
29) 1-(fluorenyl)-2-(cyclopentadienyl) ethane zirconium dichloride,
30) 1-(fluorenyl)-3-(cyclopentadienyl) propane zirconium dichloride;
31) 1-(fluorenyl)-1-(cyclopentadienyl)-1,1-(diphenyl) germanyl zirconium dichloride,
32) 1-(fluorenyl)-1-(cyclopentadienyl)-1,1-(dimethyl) silylene zirconium dichloride,
33) 1,1-bis(fluorenyl)-1,1-(dimethyl) silylene zirconium dichloride, also sometimes referred to as bis(fluorenyl)-dimethyl silyl zirconium dichloride or bis(fluorenyl) (dimethyl) silane zirconium dichloride.
34) 1-(fluorenyl)-1-(cyclopentadienyl)-1-(methyl) aluminum zirconium dichloride,
35) bis(1-methylfluorenyl)-(dimethyl) tin zirconium dichloride,
36) bis(1-methylfluorenyl)-(diphenyl) tin zirconium dichloride,
37) bis(1-methylfluorenyl)-(dimethyl) silylene zirconium dichloride,
38) 1,2-di(3,4-benzofluorenyl) ethane zirconium dichloride, and
39) 1-(3,4-benzofluorenyl)-1-(cyclopentadienyl)-1,1-(dimethyl) methane zirconium dichloride.

Other examples of bridged fluorenyl-containing metallocenes include those disclosed in published European Application No. 574,258, the disclosure of which is incorporated herein by reference. Still other bridged fluorenyl-containing metallocenes include the fluorenyl-containing metallocenes of formula Ia of published Canadian Patent Application No. 2,069,602, and those disclosed in U.S. Pat. No. 5,281,679, the disclosures of which are incorporated herein by reference. Still other examples include compounds similar to those of the formulas disclosed in U.S. Pat. No. 5,324,800, column 4, lines 23–25, wherein the metallocenes differ in that at least one ($C_5R'_m$) is a fluorenyl-containing radical.

Although not being bound by any theory, it may be that the results being observed when these metallocenes are used to polymerize ethylene are due to the fact that these specific fluorenyl-containing metallocenes have such good comonomer incorporation under the specified polymerization conditions that when small amounts low molecular weight polymer containing terminal vinyl groups are formed they are readily incorporated as side chains into the higher molecular weight polymer that is either present or being formed. The side chains are believed to generally be uniformly distributed.

Examples of suitable cocatalysts include generally any of those organometallic cocatalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. Other examples of known cocatalysts include the use of a stable non-coordinating counter anion cocatalyst, an example of such is disclosed in U.S. Pat. No. 5,155,080, e.g. using triphenyl carbenium tetrakis (pentafluorophenyl) boronate. Another example would be the use a mixture of trimethylaluminum and dimethylfluoroaluminum such as disclosed by Zambelli et al, *Macromolecules*, 22, 2186 (1989). In such counter anion systems the cocatalyst can be viewed as an ion-exchange compound comprising a cation which will irreversibly react with as least one ligand contained in the metallocene and a non-coordination anion which is ether a single coordination complex comprising a plurality of lipophilic radicals covalently coordinated to and shielding a central formally charge-bearing metal or metalloid atom or an anion comprising a plurality of boron atoms such as polyhedral boranes, carboranes, and metallacarboranes.

The currently most preferred cocatalyst is an aluminoxane. Such compounds include those compounds having repeating units of the formula

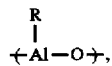

where R is generally a hydrocarbyl group having 1 to 5 carbon atoms.

Aluminoxanes, also sometimes referred to as poly (hydrocarbyl aluminum oxides) are well known in the art and are generally prepared by reacting an hydrocarbylaluminum compound with water. Such preparation techniques are disclosed in U.S. Pat. Nos. 3,242,099 and 4,808,561, the disclosures of which are incorporated herein by reference. The currently preferred aluminoxane cocatalysts are prepared either from trimethylaluminum or triethylaluminum and are sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

In a particular preferred embodiment, the bridged sandwich bonded fluorenyl metallocene is employed in combination with a solid organoaluminoxane which is substantially insoluble in the polymerization diluent under particle form polymerization conditions. Such a solid aluminoxane can be prepared by contacting a solution of an organoaluminoxane with an organoboroxine under conditions sufficient to produce a solid. Another technique for preparing an insoluble organoaluminoxane involves contacting a solution of an organoaluminoxane with water or an active hydrogen compound as taught in U.S. Pat. No. 4,990,640.

Still another technique of producing a solid cocatalyst involves contacting an organoaluminoxane with an organic borane compound free of acidic hydrogen as taught in U.S. patent application Ser. No. 08/080,899 filed Jun. 22, 1993, now U.S. Pat. No. 5,354,721, the disclosure of which is incorporated herein by reference. Yet another technique involves contacting an organoaluminoxane with an organoboron compound having boron acid functionality, i.e. —BOH, as taught in U.S. patent application Ser. No. 08/092,143 filed Jul. 14, 1993, now U.S. Pat. No. 5,414,180, the disclosure of which is incorporated herein by reference.

The currently preferred technique for preparing the solid organoaluminoxy cocatalyst involves contacting an organic solution of an organoaluminoxane optionally containing trialkylaluminums with a suitable organoboroxine compound as taught in U.S. patent application Ser. No. 08/017,207 filed Feb. 12, 1993, now U.S. Pat. No. 5,411,925, the disclosure of which is incorporated herein by reference.

Various boroxines are known in the art. The term organo boroxine as used herein refers to compounds of the formula (RBO) wherein each R is the same or a different organo group free of hydroxyl (HO—) or mercapto (HS—) groups. The R groups could include such radicals as methyl, ethyl, isopropyl, tertiary butyl, 2-ethyl ethylene, tri-n-butyl methyl, o-tolyl, phenyl, o-tri-fluoro methyl phenyl, o-chloro-phenyl, 2,6-dimethyl phenyl, $C_2H_5$—S— $CH_2CH_2CH_2$—, $CH_2$=CH—$CH_2$—, α-naphthyl, β-naphthyl, and the like. The R groups could also be R'O—, R'S—, R'$_2$N—, R'$_2$P—, and R'$_3$Si— wherein each R' is a hydrocarbyl group. Generally each R group contains about 1 to about 25 carbon atoms, more typically 1 to 10 carbon atoms. Especially preferred are the hydrocarbyl boroxines and the hydrocarbyl oxy boroxines. Examples of hydrocarbyl boroxines include trimethyl boroxine, triethyl boroxine, tri-n-propyl boroxine, tributyl boroxine, tricyclohexyl boroxine, triphenyl boroxine, methyl diethyl boroxine, dimethylethyl boroxine, and the like. The currently preferred hydrocarbyl boroxines are trimethyl boroxine and triethyl boroxine. The term hydrocarbyloxy boroxine refers to compounds of the formula ((R'O)BO) wherein each R' can be the same or different hydrocarbyl group, generally containing about 1 to about 10 carbon atoms. Trialkyloxy boroxines are currently preferred. Trimethoxy boroxine is an example.

The reaction of the boroxine with the aluminoxane can be carried out in any suitable manner. One particularly desirable technique simply involves contacting the two reactants in a suitable liquid diluent. One preferred technique involves contacting a hydrocarbon solution of the aluminoxane with a hydrocarbon solution of the boroxine. Another technique involves contacting a hydrocarbon solution of the aluminoxane with a countersolvent to produce a slurry comprising soluble aluminoxane and insoluble particulate aluminoxane and then contacting the resulting slurry with a solution of the boroxine. It is also within the scope of the present invention to carry out the reaction of the boroxine and the aluminoxane in the presence of a particulate diluent so that the insoluble product becomes deposited upon the particulate diluent. Typical particulate diluents would include such inorganic materials as silica, alumina, aluminum phosphate, silica-alumina, titania, kaolin, fumed silica, and the like.

It is also within the scope of the present invention to prepare the inventive particulate organo-aluminoxy composition and then combine it with a solution of a trialkylaluminum compound, e.g. trimethylaluminum or others of the type mentioned above, and then to contact the resulting slurry with additional boroxine of the type described above. It is believed that this process may provide a method for further increasing the molecular weight of the particulate aluminoxy composition that is initially produced by reacting the aluminoxane with the boroxine. Obviously, such a process could be repeated several times to obtain the desired level of molecular weight, particle size, bulk density, or other characteristic that is desired for a particular application.

The amount of boroxine employed relative to the aluminoxane can vary over a wide range depending upon the particular results desired. A technique which has been used in this invention for reflecting the ratio of boroxine to aluminoxane, involves the use of a calculated amount for the amount of aluminoxy aluminum in the aluminoxane solution. As used herein the term calculated aluminum is the value obtained by using a vacuum to strip the solvent off a known volume of the aluminoxane solution; weighing the recovered solid; and dividing the weight of the solid per milliter by the average molecular weight of the aluminoxy units,

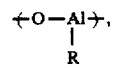

i.e. 58 for methylaluminoxane, so that one obtains a calculated value for the number of moles of aluminum per volume of the aluminoxane solution that is to be reacted with the boroxine. It is theorized that a substantial portion of any free trihydrocarbyl aluminum in the aluminoxane solution is removed when the solvent is stripped off. Any trihydrocarbyl aluminum that is present in the solid recovered after the vacuum stripping, is not considered to have a significant effect upon the calculated aluminum value. Using this method, the atomic ratio of the boron in the boroxine to calculated Al in the aluminoxy units of the aluminoxane employed will be in the range of about 1/20 to about 1/3, more preferably about 1/15 to about 1/5, still more preferably about 1/7. As noted above, the commercial aluminoxane solutions generally contain at least some trihydrocarbyl aluminum, in addition to aluminoxy units. Generally, the trihydrocarbyl aluminum accounts for about about 0.1 to about 35 weight percent of the aluminum in the solution. It is generally preferred for the boroxine to be employed in such an amount that the molar ratio of the boroxine to the trihydrocarbyl aluminum be at least about 0.3334/1.

The metallocene catalyst systems of this invention are particularly useful for the polymerization of ethylene, either alone or with another olefin comonomer. Typically the comonomer is an olefin containing 3 to 30 carbon atoms, more commonly 4 to 12 carbon atoms. Examples of olefin comonomers include propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3-4-dimethyl-1-hexene, and the like and mixtures thereof. The amout of comonomer employed can vary over a wide range depending upon the particular results desired. A particularly interesting type of copolymer is produced when the monomers are employed in amounts such that the molar ratio of the ethylene employed to the comonomer employed is at least about 1 to 1. Interesting copolymers are also obtained when ethylene and an alpha olefin having 4 to 12 carbon atoms are employed in amounts such that the molar ratio of the comonomer employed to the ethylene employed is in the range of about 0.001 to 1 to about 0.5 to 1, more typically in the range of about 0.025/1 to about 0.5/1.

The polymerizations can be carried out under a wide range of conditions depending upon the particular metallocene catalyst system employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

The polymerizations can be carried out using a homogeneous catalyst system in which the catalyst and cocatalyst are soluble; however, it is also within the scope of the present invention to carry out the polymerizations in the presence of solid forms of the catalyst and/or cocatalyst. The metallocene and/or the cocatalyst can be employed on a solid insoluble support, i.e. silica.

When an aluminoxy cocatalyst is employed generally the molar ratio of the aluminum in the organoaluminoxy cocatalyst to the transition metal in the metallocenes would be in the range of about 1:1 to about 100,000:1 and more preferably about 5:1 to about 15,000:1. As a general rule, the polymerizations would be carried out in the presence of liquid diluents which do not have an adverse affect upon the catalyst system. Examples of such liquid diluents include propane, butane, isobutane, pentane, hexane, heptane, octane, cyclohexane, methylcyclohexane, toluene, xylene, and the like. The polymerization temperature can vary over a wide range, temperatures typically would be in the range of about $-60°$ C. to about $300°$ C., more preferably in the range of about $20°$ C. to about $160°$ C. Particularly preferred for slurry or particle form polymerization are temperatures in the range of from about $60°$ C. to about $120°$ C. The pressure can also vary over a wide range. Typically the pressure would be in the range of from about 1 to about 500 atmospheres or greater.

The polymers produced with this invention have a wide range of uses that will be apparent to those skilled in the art from the physical properties of the respective polymer. In accordance with the present invention it is possible to obtain polymers of ethylene having a density of at least about 0.93 g/cc and a flow activation energy greater than 25 kJ/mol. An even more preferred type of polymer that can be produced in accordance with the present invention has a flow activation energy of at least about 30 kJ/mol and a weight average molecular weight of at least 30,000, and HI in the range of 2 to 20, and a density of at least about 0.94 g/cc. A further understanding of the present invention and its objects and advantages will be provided by a review of the following specific examples.

In the examples which follow, the polymerizations were conducted in a one gallon stirred autoclave reactor. The technique for the polymerizations involved combining the catalyst system with about 2 liters of isobutane in the reactor at ambient temperature. In some cases, the reactor was also charged with a known amount of hydrogen as determined by the pressure drop from a 300 cc pressure vessel. In the tables that follow, the hydrogen level is reported in terms of psi based on that pressure drop. The reactor was then brought to the desired polymerization temperature and the ethylene was added. The reactor was then typically maintained at that temperature for about 60 minutes. Then the isobutane was vented from the reactor and the polymer was collected as a dry fluff.

In runs which employed a comonomer, hexene-1 was added in a known amount before the reactor was brought to the polymerization temperature. In the tables the amount of comonomer reported is in grams. In the runs which used a solid aluminoxy cocatalyst, the metallocene and the solid aluminoxy cocatalyst were first mixed together overnight in hexane. The resulting solid was then washed, filtered, and dried under vaccum. The resulting solid catalyst system comprising the metallocene and the solid aluminoxane was then added to the polymerization autoclave.

Various characteristics of the polymer and the polymerization were characterized. Examples of characteristics determined in various cases include density in grams/mL (ASTM D1505-68); High Load Melt Index (HLMI) in grams of polymer/10 minute $190°$ C. (ASTM D1238, Condition 190/21.6); Melt Index (MI) in grams of polymer/10 minute $190°$ C. (ASTM D1238, Condition 190/2.16); Shear Stress Response (SR) determined by dividing HLMI by MI; Molecular weights by size exclusion chromatography, i.e. weight averge molecular weight referred to herein as $M_w$; and number average molecular weight referred to herein as $M_n$; and heterogenity index (HI) determined by dividing $M_w$ by $M_n$. The (SEC) size exclusion chromatography was conducted using a linear column capable of resolving the wide range of molecular weights generally observed in polyolefins, such as polyethylene.

The property referred to herein as flow-activation energy, also sometimes referred to as energy of activation, i.e. Ea, reflects the sensitivity of polymer melt viscosity to temperature. This is generally viewed as a function of the linear vs network character of the polymer. The molecular weight, the molecular weight distribution, and the degree of chain entanglement are also generally viewed as factors affecting the flow activation energy. The Ea in terms of kJ/mol can be readily determined from data obtained using a dynamic rheometer such as Rheometrics Inc. (RMS 800) dynamic rheometer. A standard prescription for summarizing the viscosity-temperature dependence of polymer melts has long been available in the scheme known as the Williams-Landel-Ferry (WLF) time-temperature superposition which is described in the classic text entitled "Viscoelastic Properties of Polymers", 3rd Edition (John Wiley & Sons, New York, 1980) by John D. Ferry. Data needed for establishing the temperature dependence of dynamic viscosity, also referred to as complex viscosity, versus frequency, or viscosity vs shear rate, are not difficult to obtain at various temperatures in a range between melting and the onset of chemical degradation. In order to ensure that the Ea values are most accurate, it is desirable to optimize the data to produce optimally smooth isothermal master curves according to the WLF time-temperature superposition but using a least squares closeness-of-fit criterion based on Carreau-Yasuda model parameters that have been shown previously to give highly precise fits to single temperature polyethylene data. This can be done in various ways. The currently preferred technique involves subjecting the dynamic viscosity frequency curves obtained at various temperatures using a Rheometrics, Inc. dynamic viscometer to a proprietary computer program entitled "Rheology Analysis Program CY" covered by Phillips Petroleum Company unpublished copyright which was filed for registration on Jan. 31, 1995. This proprietary computer program is available for use by others under a licensing program.

Discussions of the Carreau-Yasuada model can be found in *Dynamics of Polymeric Liquids*, Second ed. (John Wiley & sons, New York, 1987) by R. Byron Bird, Robert C. Armstrong, and Ole Hassager; as well in C. A. Hieber and H. H. Chiang, "Some Correlations Involving the Shear Viscosity of Polystryrene Melts,", *Rheol. Acta*, 28, 321–332 (1989) and in C. A. Hieber and H. H. Chiang, "Shear-Rate-Dependence Modeling of Polymer Melt Viscosity.", *Polym. Eng. Sci*, 32, 031–938 (1992).

The property referred to herein as zero-shear melt viscosity, eta 0, also sometimes referred to as $\eta_o$, is determined at 190° C. using the complex viscosity data from a Rheometrics dynamic spectrometer. The $\eta_o$ value can be rized in Table I of this disclosure.

TABLE I

| Run | H$_2$ | C$_6$/C$_2$ | Hexene, g | Cat., mg | MI | Density | M$_w$/1000 | HI | SR | Ea |
|---|---|---|---|---|---|---|---|---|---|---|
| 1 | 10 | 0 | 0 | 0.026 | 0.1 | 0.9587 | 130.8 | 7.32 | 128.3 | 34.7 |
| 2 | 10 | 0.129 | 45 | 0.0195 | 2.14 | 0.9298 | 66.2 | 6.6 | 42.2 | 29.3 |
| 3 | 10 | 0.24 | 90 | 0.195 | 3.98 | 0.9176 | 61.2 | 4.12 | 38.2 | 29.9 | obtained using the aforementioned computer program entitled "Rheology Analysis Program CY" which implements methods of the type described in the aforementioned papers by C. A. Hieber and H. H. Chiang. The units of $\eta_o$ are Pascal seconds, i.e. Pa.s.

EXAMPLE I

The polymerization of Run 14 of applicants' commonly owned copending case Ser. No. 07/734,853 employed 1-(9-fluorenyl)-1-(cyclopentadienyl) methane zirconium dichloride and methylaluminoxane as the catalyst system at 70° C. The ethylene polymer product of that Run 14 had a density of 0.8817 g/cc, a flow activation energy of 60.6 kJ/mol and a zero shear melt viscosity, i.e. eta 0, of 4.2×10$^5$Pa.s. Other properties of that polymer are listed in Table II of the 734,853 application.

As noted therein, that polymer can be referred to as a low density super random copolymer. It contained about 12.4 mole percent comonomer and had a relative comonomer dispersity of 105.9 and a M$_w$ of about 42,700.

EXAMPLE II

The polymerization of Run 11 of applicants' copending case Ser. No. 07/734,853 employed 1-(9-fluorenyl)-2-(indenyl) ethane zirconium dichloride and methylaluminoxane as the catalyst system at 70° C. The ethylene polymer product of that Run 11 had a density of 0.9727 g/cc and a flow activation energy of 26.8 kJ/mol. Other properties of that polymer are listed in Table II of the 734,853 application.

EXAMPLE III

Another series of polymerization runs were carried out at 90° C. using a catalyst system consisting of 1-(9-fluorenyl) -2-(indenyl) ethane zirconium dichloride and a solution of methylaluminoxane. The comonomer hexene-1 was used in two of the runs. The polymerization variables and various properties of the resulting ethylene polymers are summarized in Table I of this disclosure.

Run 1 of Table I demonstrates that even though no comonomer was employed a polyethylene was obtained that had an unusually high Ea, evidence of branching. The two copolymers also had unusually high Ea values for such narrow molecular weight products. The polymer of Run 1 is particularly unusual in that it has Ea, density, and a molecular weight spectrum substantially the same as a commercial ethylene-hexene copolymer produced using a chromium catalyst. The commercial Cr polymer is generally used in HIC (Household Industrial Container) applications. The fact that the polymer of Run 1 had a much higher Ea than that of the polymer of Example II may be due in part to the difference in molecular weight or to the higher polymerization temperature used in Run 1, the higher temperature being believed to favor the copolymerization of higher olefin species.

EXAMPLE IV

Another series of runs was carried out at 90° C. using a catalyst system consisting of 1-(9-fluorenyl)-1-(indenyl) ethane zirconium dichloride and a solid hydrocarbyl aluminoxy cocatalyst prepared by reacting methylaluminoxane with an organoboroxine as taught in commonly owned application Ser. No. 08/017,207(issued as U.S. Pat. No. 5,411,925). The polymerization variables and various properties of the polymers of the polymerization runs are summarized in Table II.

TABLE II

| Run | H$_2$ | C$_6$/C$_2$ | Hexene, g | Cat., mg | MI | Density | M$_w$/1000 | HI | SR | Ea | $\eta_o$/10$^5$ |
|---|---|---|---|---|---|---|---|---|---|---|---|
| 4 | 3 | 0.025 | 5 | 0.0848 | 0.15 | 0.9504 | 157.8 | 5.5 | 48.1 | 29.9 | 1.15 |
| 5 | 3 | 0.039 | 10 | 0.091 | 0.08 | 0.9646 | 144.1 | 3.5 | 93.1 | 32.6 | 12.3 |
| 6 | 3 | 0.069 | 20 | 0.1039 | 0.04 | 0.9387 | 148.6 | 4.1 | 124.2 | 33.5 | 4.28 |
| 7 | 3 | 0.123 | 40 | 0.0795 | 0.12 | 0.9298 | 153.8 | 3.4 | 46.2 | 35.8 | 43.4 |
| 8 | 3 | 0.263 | 90 | 0.1026 | 0.02 | 0.8808 | 147.6 | 2.7 | 149 | 39.7 | 3.5 E + 03 |
| 9 | 3 | 0.404 | 140 | 0.1069 | 0.1 | 0.8906 | 142 | 3.5 | 106 | 43 | 3.9 E + 05 |

Table II demonstrates that the catalyst system comprising the metallocene supported on a solid hydrocarbyl aluminoxane is effective in producing copolymers having a wide density range, i.e. 0.8808 to 0.9646 g/cc, using hexene to ethylene molar ratios in the reactor in the range of 0.025/1 to 0.404/1. The copolymers also showed unusually high Ea for polymers having those molecular weights and molecular weight distributions. The data also show that increasing the level of comonomer increases the Ea and the zero shear viscosity, i.e. $\eta_o$.

EXAMPLE V

Another series of polymerizations was carried out at 90 ° C. using a catalyst system consisting of 1-(3-propy-1-enyl)

indenyl)-1-(9-fluorenyl) dimethyl silane zirconium dichloride and a solid hydrocarbyl alnminoxy cocatalyst of the type used in Example IV. The polymerization variables and various properties of the polymers produced are summarized in Table III.

TABLE III

| Run | $H_2$ | Hexene, g | Cat., mg | MI | Density | $M_w/1000$ | HI | SR | Ea |
|---|---|---|---|---|---|---|---|---|---|
| 10 | 3 | 0 | 0.1319 | 0.1 | 0.9505 | 131 | 16.5 | 54 | 30.2 |
| 11 | 3 | 5 | 0.1319 | 0.57 | 0.9486 | 91 | 4.1 | 35 | 34.8 |
| 12 | 3 | 10 | 0.1348 | 0.01 | 0.9388 | 184 | 3.2 | 221 | 34.8 |
| 13 | 3 | 10 | 0.1449 | 0.02 | 0.9356 | 144 | 18.1 | 247 | 31.8 |
| 14 | 3 | 20 | 0.1443 | 0.1 | 0.9312 | 129 | 2.9 | 43 | 36.1 |
| 15 | 3 | 40 | 0.1369 | 0.02 | 0.9146 | 120 | 2.4 | 258 | 43.2 |
| 16 | 3 | 90 | 0.1418 | 0.21 | 0.911 | 114 | 3 | 66 | 43.1 |
| 17 | 3 | 140 | 0.1528 | 0.42 | 0.9026 | 68 | 9.4 | 69 | 40.8 |

Here again the tests reveal the polymers have high flow activation energies for polymers produced with metallocenes.

EXAMPLE VI

Still another series of polymerizations was carried out at 90° C. using a catalyst system consisting of 1-(9-fluorenyl)-1-(1-indenyl) methane zirconium dichloride and a solid hydrocarbyl aluminoxy cocatalyst of the type used in Example IV. The polymerization variables and various properties are summarized in Table IV.

TABLE IV

| Run | $H_2$ | Hexene, g | Cat., mg | MI | Density | $M_w/1000$ | HI | SR | Ea |
|---|---|---|---|---|---|---|---|---|---|
| 18 | 3 | 0 | 0.1 | 0.76 | — | — | — | 21 | — |
| 19 | 3 | 5 | 0.161 | 0.48 | 0.9607 | 67.5 | 13.4 | 78 | (40.8) |
| 20 | 3 | 10 | 0.138 | 0.41 | 0.9569 | 66.1 | 6 | 148 | (46.3) |
| 21 | 3 | 20 | 0.152 | 4.03 | 0.9462 | 52.5 | 3.9 | 25 | — |
| 22 | 3 | 40 | 0.153 | 12.98 | — | 46.8 | 3.9 | 31 | — |
| 23 | 3 | 90 | 0.21 | 10.26 | 0.9351 | 45.6 | 6.8 | — | — |
| 24 | 3 | 140 | 0.19 | 208.6 | 0.9091 | 30.2 | 4.8 | — | — |

The Ea values reported for Runs 19 and 20 are reported in parentheses because there were signs of gel in the polymer samples which leads to the conclusion that the amount of branching is even greater than reflected by the Ea values determined from the polymers. The results indicate much higher degrees of branching than one would have expected for polymers produced with a metallocene. Flow activation determinations for the polymers of Runs 21–24 were not carried out since the levels of gel observed were considered too high to permit meaningful rheology tests to be carried out. It thus appears that at lower densities it is even possible to produce polymers which have some properties similar to free radical modified polyethylenes.

EXAMPLE VII

Another series of polymerizations were carried out using a catalyst system consisting of 1-(but-3-enyl)-1-(cyclopentadienyl)-1-(9-fluorenyl)-1-(methyl) methane zirconium dichloride and a solid hydrocarbyl aluminoxy cocatalyst of the type used in Example IV. The polymerization variable and various polymer properties are summarized in Table V. In these runs the polymerization temperature was 80° C.

TABLE V

| Run | $H_2$ | Hexene, g | Cat., mg | MI | SR | Density | $M_w/1000$ | HI | Ea | $\eta_o/10^4$ |
|---|---|---|---|---|---|---|---|---|---|---|
| 25 | 20 | 5 | 0.00077 | 0.86 | 39 | 0.9475 | 155 | 6.19 | 27.5 | 2.09 |
| 26 | 20 | 20 | 0.00077 | 0.86 | 57 | 0.9385 | 112 | 14.3 | 30.3 | 2.02 |
| 27 | 20 | 40 | 0.00077 | 0.2 | 693 | 0.9288 | 105 | 5.19 | 40.9 | 2.61 |

Here again the polymers had an unusually high flow activation energy for polymers produced with a metallocene. These polymers were evaluated using FTIR and it was discovered that the number of vinyl end groups was in the range of 0.26 to 0.69 per 1000 carbon atoms, with the number of vinyl groups increasing as the molecular weight decreased. This was in contrast to the number of vinyl groups noted for polymers prepared using the 1-(9-fluorenyl)-2-(indenyl) ethane zirconium dichloride for which the number of vinyl groups per 1000 carbon atoms were in the range of 0.06 to 0.14.

EXAMPLE VIII

By way of comparison a polymerization was carried using the same type of technique employed in Example IV but in this case using a non-bridged, non-fluorenyl-containing metallocene. The catalyst system was bis (n-butyl cyclopentadienyl) zirconium dichloride and a solid aluminoxy cocatalyst of the type used in Example IV. The polymerization was carried out at 90° C. using ethylene without comonomer. The liquid diluent was isobutane. The amount of hydrogen was 40 psi. The resulting polyethylene had a Weight Average Molecular Weight of 96,000; an HI of 12.4; a density of 0.9626 g/cc; a Tm(C) of 12.377; an MI of 1.1 g/10 min; an eta 0 of $6.01 \times 10^3$; and a Flow Activation Energy, i.e. Ea, of 21.6 kJ/mol. This Ea value shows that the polyethylene is a substantially linear polymer, in contrast to the ethylene polymers produced in accordance with the present invention which had Ea values greater than 25.

That which is claimed:

1. A process for preparing a polymer of ethylene having a flow activation energy of at least about 25 kJ/mol, comprising contacting ethylene in a liquid diluent with a catalyst system comprising:
   (1) a catalyst comprising 1-(9-fluorenyl)-2-(indenyl) ethane zirconium dichloride, and
   (2) a cocatalyst for said metallocene.

2. A process according to claim 1 wherein said cocatalyst comprises an aluminoxy co-catalyst having repeating units of the formula

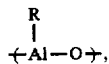

wherein, R is a hydrocarbyl group.

3. A process according to claim 2 which produces a polymer of ethylene having a density of less than 0.92 g/cc and a flow activation energy of at least 35 kJ/mol.

4. A process according to claim 1 wherein said polymerization is conducted at a temperature in the range of about 60° C. to about 111° C. in a liquid diluent consisting essentially of isobutane.

5. A process according to claim 4 wherein ethylene is polymerized in the absence of comonomer to produce a polymer having a flow activation energy of at least about 30, weight average molecular weight of at least 30,000, an HI in the range of 2 to 20, and a density of at least about 0.94 cc/g.

6. A process according to claim 4 wherein ethylene is polymerized in the presence of an acyclic comonomer having 4 to 12 carbon atoms.

7. A process according to claim 4 wherein ethylene is copolymerized with hexene-1.

8. A process according to claim 7 wherein said cocatalyst is a solid hydrocarbyl aluminoxy cocatalyst prepared by reacting methylaluminoxane and an organoboroxine.

9. A process for preparing a polymer of ethylene having a flow activation energy of at least about 25 kJ/mol comprising contacting ethylene in the presence of an acyclic olefinic comonomer having 4 to 12 carbon atoms in a liquid diluent wherein the molar ratio of the comonomer employed to the ethylene employed is in the range of from about 0.025/1 to about 0.5/1 and the resulting copolymer has a density in the range of 0.88 to about 0.96 g/cc using a catalyst system comprising:
   (1) a fluorenyl-containing metallocene selected from compounds of the formula (Z)—R'—(Z')MeQ$_2$ wherein R' is selected from —CH$_2$CH$_2$—, —CH$_2$—, and dimethylsilylene, and each Q is a halide, Z is a substituted or unsubstituted fluorenyl radical, Z' is a substituted or unsubstituted fluorenyl radical, a substituted or unsubstituted indenyl radical, a substituted or unsubstituted cyclopentadienyl radical, a tetrahydroindenyl radical, or an octahydrofluorenyl radical; Me is selected from Zr and Hf, and
   (2) a cocatalyst for said metallocene.

10. A process according to claim 9 wherein said cocatlyst comprises an aluminoxy co-catalyst having repeating units of the formula

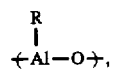

wherein R is a hydrocarbyl group.

11. A process according to claim 9 wherein Me is Zr.

12. A process according to claim 11 wherein R' is dimethylsilylene.

13. A process according to claim 9 wherein said catalyst comprises 1-(9-fluorenyl)-1-(cyclopentadienyl) methane zirconium dichloride.

14. A process according to claim 9 wherein said catalyst comprises 1-(9-fluorenyl)-2-(indenyl) ethane zirconium dichloride.

15. A process according to claim 9 wherein said catalyst comprises 1-(9-fluorenyl)-1-(indenyl) dimethyl silane zirconium dichloride.

16. A process according to claim 9 wherein said catalyst comprises bis 1,2-(9-fluorenyl) ethane zirconium dichloride.

17. A process according to claim 9 wherein said catalyst comprises 1-(9-fluorenyl)-1-(3-prop-1-enyl indenyl) dimethyl silane zirconium dichloride.

18. A process according to claim 9 wherein Z' is selected from substituted or unsubstituted indenyl.

19. A process according to claim 11 wherein Z' is selected from substituted or unsubstituted indenyl.

20. A process according to claim 9 wherein the molar ratio of comonomer employed to ethylene employed is in the range of from about 0.025/1 to about 0.5/1 and the resulting copolymer has a molecular weight of at least about 30,000 and a density in the range of from about 0.88 to about 0.96 g/cc.

21. A process according to claim 9 wherein ethylene is copolymerized with hexene-1.

22. A process according to claim 21 wherein said copolymerization is conducted at a temperature in the range of about 60° C. to about 111° C. and the liquid diluent consists essentially of isobutane.

23. A process according to claim 22 which produces a polymer of ethylene having a flow activation energy in the range of about 30 to about 60 kJ/mol and a density of less than 0.92 g/cc.

24. A process according to claim 23 which produces a polymer of ethylene having an HI of 6 or less.

25. A process according to claim 23 which produces a polymer of ethylene having an HI greater than 6 and less than 20.

* * * * *